(12) United States Patent
Mahfoud Familia et al.

(10) Patent No.: US 8,729,472 B2
(45) Date of Patent: May 20, 2014

(54) SYSTEMS AND METHODS FOR PERMEABILITY RATE TESTING OF BARRIER FILMS

(75) Inventors: Aziz Mahfoud Familia, Shrewsbury, MA (US); David Shackleford, Framingham, MA (US); Nafih Mekhilef, Northborough, MA (US); Mike Zimmerman, North Andover, MA (US)

(73) Assignee: Saint-Gobain Performance Plastics Corporation, Aurora, OH (US)

( * ) Notice: Subject to any disclaimer, the term of this patent is extended or adjusted under 35 U.S.C. 154(b) by 0 days.

(21) Appl. No.: 13/217,519

(22) Filed: Aug. 25, 2011

(65) Prior Publication Data

US 2012/0062896 A1 Mar. 15, 2012

Related U.S. Application Data

(60) Provisional application No. 61/381,827, filed on Sep. 10, 2010.

(51) Int. Cl.
*G01J 5/00* (2006.01)
*G01J 5/02* (2006.01)

(52) U.S. Cl.
USPC .................. 250/338.1; 250/339.01; 250/343

(58) Field of Classification Search
USPC .................. 250/338.1, 339.01, 343
See application file for complete search history.

(56) References Cited

U.S. PATENT DOCUMENTS

| | | | |
|---|---|---|---|
| 5,015,856 A * | 5/1991 | Gold | 250/339.09 |
| 7,369,242 B2 * | 5/2008 | Cole et al. | 356/436 |
| 2006/0181710 A1 | 8/2006 | Kachanov et al. | |
| 2007/0247753 A1 | 10/2007 | Takahashi et al. | |
| 2008/0060418 A1 | 3/2008 | Deroos et al. | |
| 2008/0084561 A1 | 4/2008 | Patel et al. | |
| 2008/0123712 A1 * | 5/2008 | Zhou et al. | 372/55 |
| 2008/0151248 A1 * | 6/2008 | Cole et al. | 356/437 |
| 2009/0133475 A1 | 5/2009 | Glock-Jager et al. | |
| 2010/0294025 A1 | 11/2010 | Omori et al. | |

FOREIGN PATENT DOCUMENTS

JP          2002-357533     *   5/2001   ............ G01N 15/08

OTHER PUBLICATIONS

"Development and Applications of Continuous-Wave Cavity Ring-Down Spectroscopy", Int. J. Thermophys (2008) pp. 1567-1577, to Yan et al.*
International Search Report PCT/US2011/049268 (3 pgs.).
International Preliminary Report on Patentability from related PCT application PCT/US2011/049268 dated Mar. 12, 2013, 5 pages.

* cited by examiner

*Primary Examiner* — David Porta
*Assistant Examiner* — Kenneth J Malkowski
(74) *Attorney, Agent, or Firm* — Fulbright & Jaworski, LLP; Scott D. Rothenberger

(57) ABSTRACT

The present invention is directed to systems and methods which utilize a cavity ring-down spectroscopy (CRDS) technique implemented for the measurements of vapor transmission rate. In one embodiment, the vapor content to be measured is contained within an optical cavity. Light is then injected into the cavity up to a threshold level and the decay time of the injected light is measured. When the wavelength of the injected light is resonant with an absorption feature of the vapor the decay time increases linearly as a function of vapor content. In this manner, vapor content causes a longer decay time and thus the amount of vapor passing through the film (film permeation rate) can be determined in real-time.

20 Claims, 6 Drawing Sheets

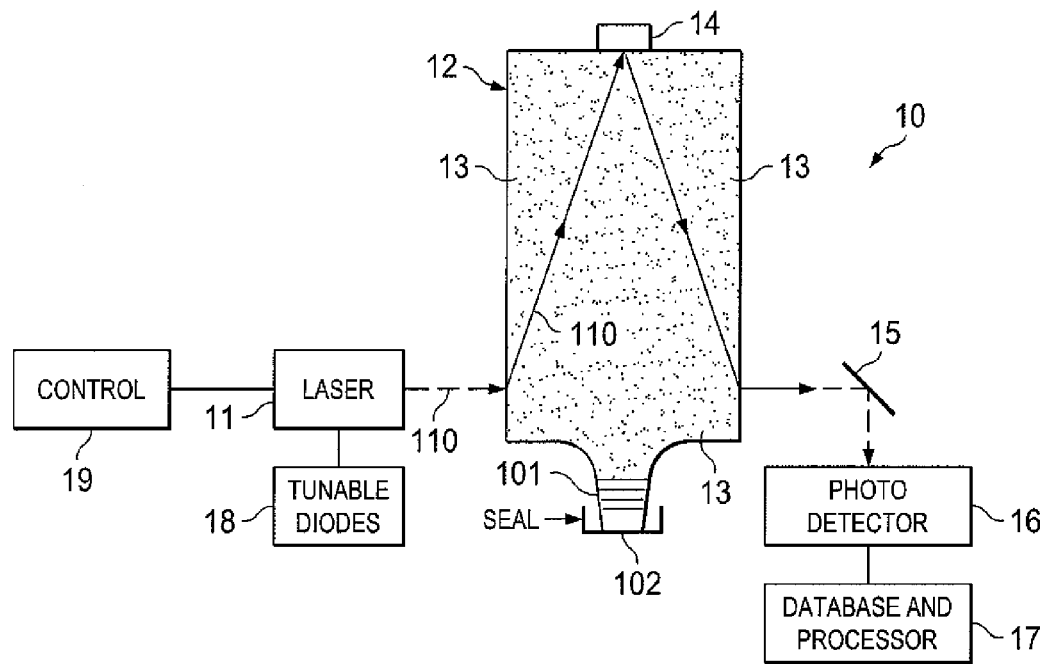
FIG. 1
FIG. 2
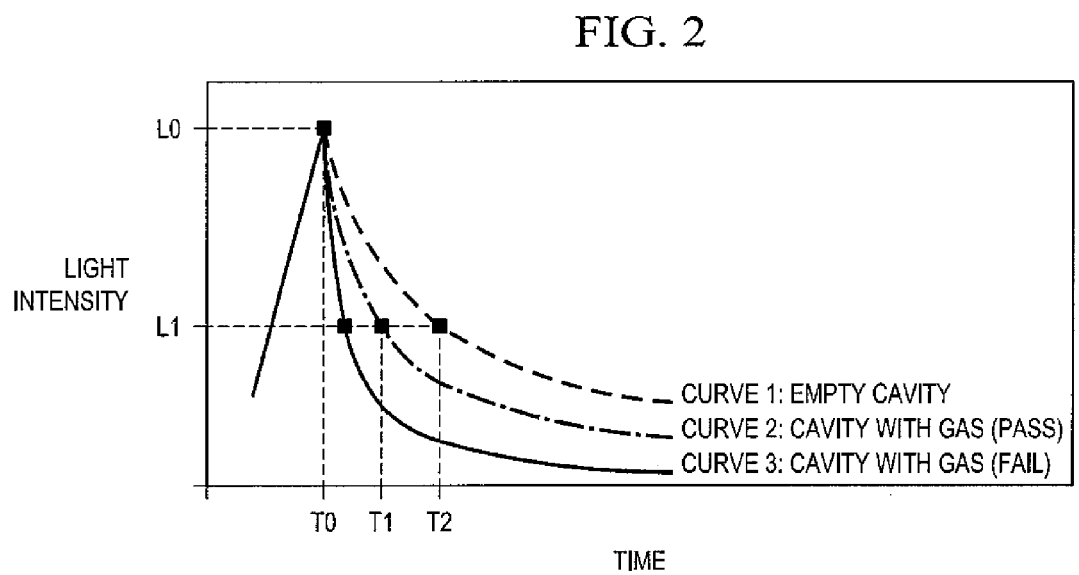

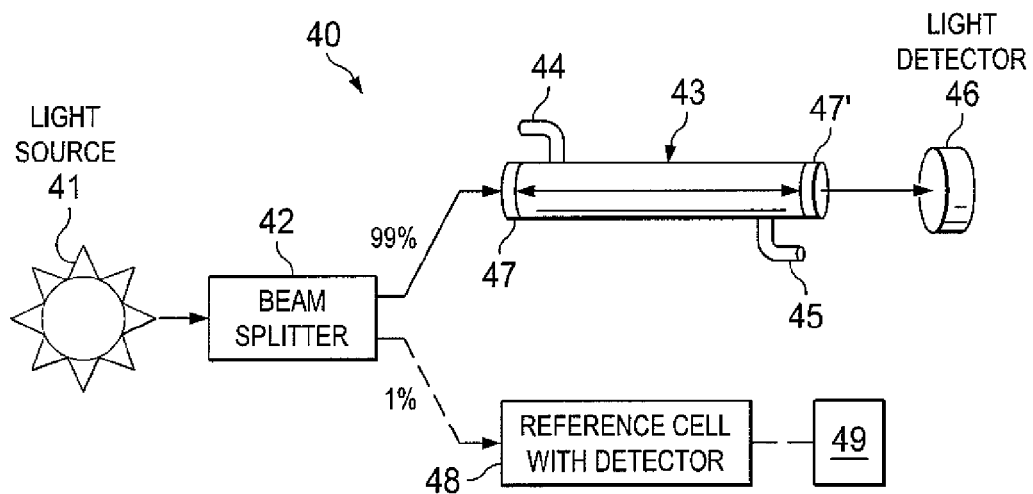
FIG. 4A
FIG. 4B
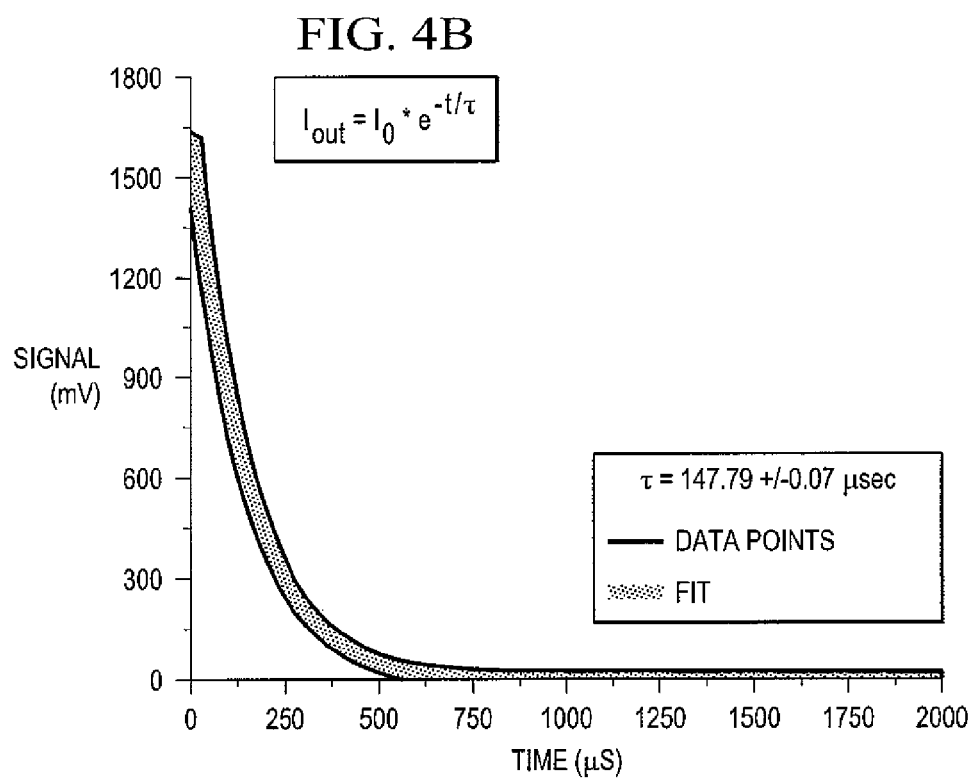

SYSTEMS AND METHODS FOR PERMEABILITY RATE TESTING OF BARRIER FILMS

CROSS-REFERENCE TO RELATED APPLICATIONS

This application claims the benefit of U.S. Provisional Application No. 61/381,827 filed on Sep. 10, 2010 and entitled, "SYSTEMS AND METHODS FOR PERMEABILITY TESTING OF BARRIER FILMS USING OPTICAL CAVITY LIGHT DECAY TIME," the disclosure of which is incorporated herein by reference.

TECHNICAL FIELD

This disclosure relates to measuring systems and more specifically to systems and methods for permeation rate testing of barrier films. Even more specifically, this disclosure relates to water vapor permeation rate testing of plastic barrier films.

BACKGROUND OF THE INVENTION

One important characteristic of certain materials, such as plastic barrier films, is the degree to which certain substances, such as gas and vapors, permeate the materials. In certain applications, such as use in photovoltaic electronic devices, low permeation rate to water vapor results in higher shelf life and thus contributes to lower cost. Water vapor transmission rate (WVTR) is a widely used measurement for determining the barrier properties of a plastic film. It is a measure of the amount of water vapor that can permeate through a certain area of a film over a certain period of time. WVTR is one of the key properties in photovoltaic, organic light emitting diodes (OLED) and other electronic devices. One target for commercialization and longevity is water vapor permeation rate in the range of $10^{-6}$ g/(m$^2$-day).

Systems, such as the Mocon Aquatran, use a coulometric phosphorus pentoxide sensor that converts water vapor to an electrical charge. Those systems can detect moisture down to the level of $5\times10^{-4}$ g/(m$^2$-day). Below this level, the coulometric technique is inadequate.

Some laboratory methods, such as the so-called calcium method, exist that can measure water vapor below $10^{-4}$ g/(m$^2$-day) using the optical transmission or the electric conductivity of a calcium coating which is encapsulated within a cell that is sealed with the barrier sample of interest. The calcium method, however, is typically laborious and the use of the method has not yet been standardized. Furthermore, the degradation of calcium is a function not only of the permeation rate of water vapor but also due to permeation of other species especially oxygen. In addition, the evidence to date does not confirm that the calcium method can actually measure WVTR as low as $10^{-6}$ g/(m$^2$-day). Thus, these systems are not sufficient for measurement of barrier properties for ultra-barriers designed for photovoltaics, OLED and other electronic devices.

Therefore, there exists a need for a gas permeation measurement technique which is simple, easy to use, has the ability to analyze for a specific molecule such as water, and has a low detection limit.

BRIEF SUMMARY OF THE INVENTION

The present invention is directed to systems and methods which utilize a wavelength-tuned cavity ring-down spectroscopy (CRDS) technique implemented for the measurements of vapor transmission rate through a barrier film. In one embodiment, the vapor content to be measured is placed within an optical cavity. Light is then injected into the cavity up to a threshold level and the decay time of the injected light is measured. When the wavelength of the injected light is resonant with an absorption feature of the vapor the decay time of the cavity decreases as a function of vapor content. In this manner, vapor content reduces decay time and thus the amount of vapor passing through the film (film permeation rate) can be determined in real-time.

In one embodiment, water vapor is measured in a pass/fail mode where the film fails if the decay time of the light is less than a threshold (high moisture content) and the film passes if the decay time is longer than a given threshold. If desired, the threshold parameters can be adjusted from time to time based on the samples being tested by other measurement techniques acting as a calibration on the production system.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 1 shows a schematic view of one embodiment of the concepts taught herein;

FIG. 2 shows decay curves for optical cavity resonant energy as a function of vapor content;

FIG. 4A shows another embodiment of the concepts discussed herein;

FIG. 4B shows the decay curve using the apparatus of FIG. 4A;

DETAILED DESCRIPTION OF THE INVENTION

Figure 3:
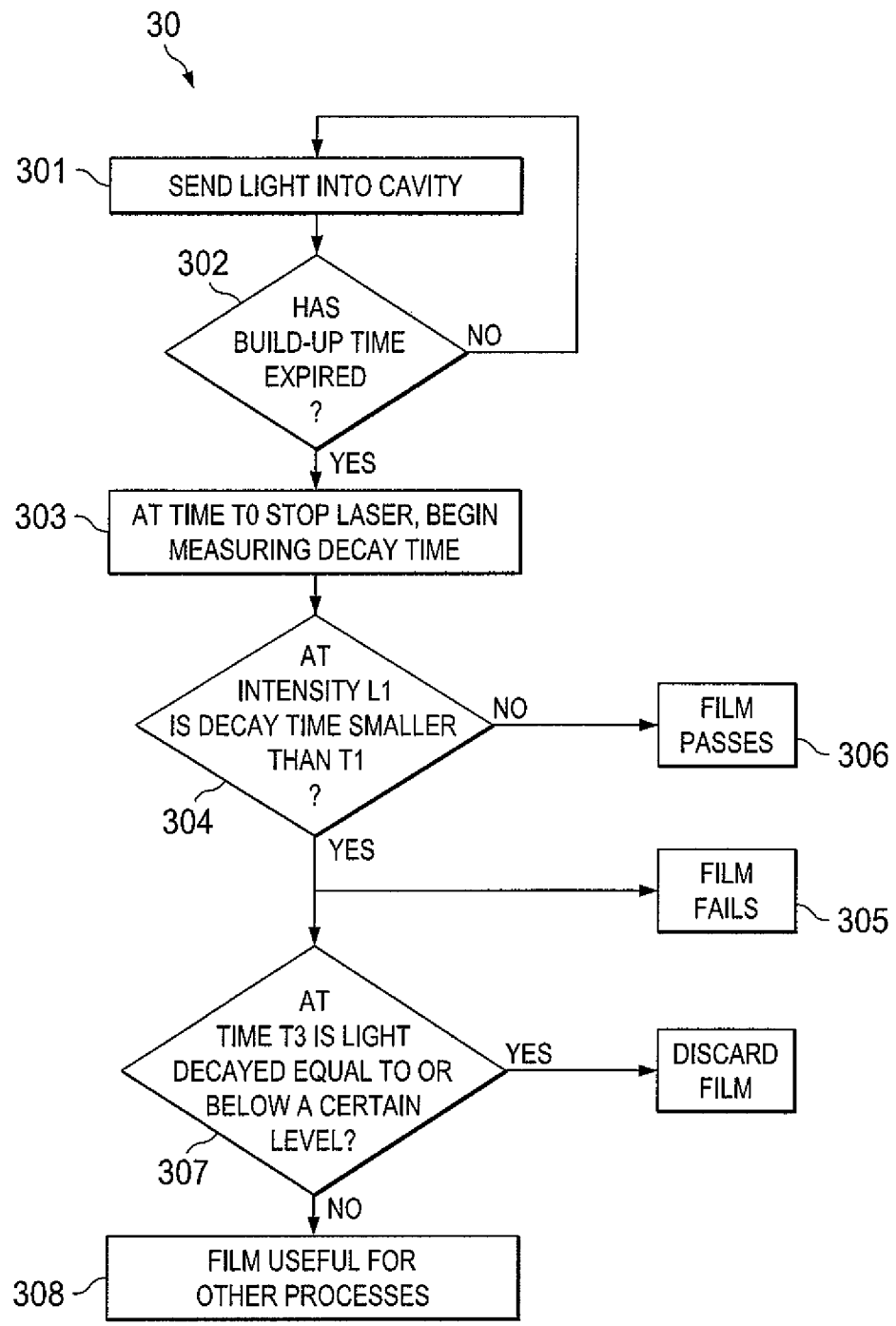
FIG. 3 is one embodiment of a method of operation of a pass/no-pass system in accordance with the inventive concepts.

Note that the discussion will be with respect to water vapor and the optics will be in terms of laser light. However, it should be noted that the concepts taught herein can be applied to other vapors such as oxygen, carbon dioxide, or methane. Oxygen for instance can be of particular importance for electronics applications. In other situations carbon dioxide, or other vapors, can be used. Also, the permeable material need not be limited to films, although films for use in photovoltaic applications are the materials and applications of first interest.

Cavity ring-down spectroscopy (CRDS) techniques for gas analysis are now known. These techniques are herein being used to measure vapor, (water vapor in our embodiments) which permeate through a film. It has been found that when the wavelength of the applied energy (laser energy in the embodiments) is set to resonate with the vapor to be detected (water vapor in the embodiments), the decay time within the optical chamber is changed. The decay time is shortened as a function of concentration of the species and with a relationship described in Table 1.

FIG. 1 shows a schematic view of one embodiment 10 of the concepts taught herein. Laser 11, governed by control circuit 19, and, if desired, tunable diodes 18, sends energy, in this embodiment in the form of laser light 110, into cavity 12 for a period of time. The laser light passes through the cavity, reflects from mirror 14 and because of the design of the cavity, at least for one embodiment, the light bounces back and forth for a period of time within the optical cavity before it exits and is reflected via mirror 15 to photodetector 16. When the laser is turned off, after a short period of time such as approximately 1 to 10 micro seconds, the photodetector continues to "see" and is able to measure the light intensity as it decays over time.

FIG. 2 shows this decay for three hypothetical situations. CURVE 1 represents the situation where no vapor is present in the optical cavity. As shown, at time T0, the light source is shut off, the light build-up ends at a level of L0 and the light then begins to decay. The lifetime of the decay is defined as the time required to reduce the initial intensity L0 to $L1=L0/e$ (where $e=2.7172...$ the natural logarithm base). The natural decay time for energy of a certain frequency (which is essentially controlled by the reflectivities of the mirrors in the cavity) is such that at time T2 the energy has decayed to a level of L1.

Now, let us assume that, as shown in FIG. 1, vapor 13 has been introduced into optical cavity 12 via input 101 (which is now sealed via temporary seal 102). The vapor causes light 110 to resonate, (at least in one embodiment) and this resonation in turn shortens the decay time of the light after time T0. This shortening of the decay time is shown in FIG. 2 CURVE 2 where at time T1, due to the vapor present in the cavity, the light intensity has decayed to level L1. If the content of vapor in the cavity corresponds to a permeation rate that is just low enough for a particular application, then the situation described by CURVE 2 where the intensity decays to level L1 at time T1 is acceptable and the film "passes." If, on the other hand, the permeation rate is too high and exceeds the acceptable threshold, then when the intensity of the cavity is equal to L1, the decay time is shorter than T1 and the film "fails" as is shown in CURVE 3.

Using this difference in decay times between situations where there is no vapor and a detectable amount of vapor, the system can calculate, as will be discussed hereinafter, the permeation rate of the film using database/processor 17 as shown in FIG. 1.

One example of a CRDS suitable for use in this system can be obtained from Tiger Optics (Warrington, Pa. as model Halo +) or from Picarro (Sunnyvale, Calif. as model G2301).

One reason for the advantages of the described system is the fact that the optical cavity yields a relatively long interaction path between the vapor sample and the optical probe (laser light) which enhances sensitivity compared to non-dispersive infrared spectroscopy, such as Fourier Transform Infrared Spectroscopy (FTIR). The system yields a cavity lifetime of 0.1 micro seconds which is equivalent to sampling a length of almost 20 km. In the case of a regular FTIR the path length is limited by the thickness of the sample, which is far less than 20 km.

Another advantage of this system is its spectral resolution capability. The mode spacing of the optical cavity has a resolution of 0.0003 $cm^{-1}$ compared with a typical FTIR of approximately 0.5 cm-1. This resolution yields linear proportional response as a function of water vapor content. Note that while visible light is used in this discussion, the concepts herein described can be used in the non-visible energy range as well.

FIG. 3 is one embodiment of a method, such as method 30, of operation of a pass/no-pass system in accordance with the inventive concepts. This method can be achieved using code-controlled applications running one or more processors, such as on processor 17 (FIG. 1). In process 301, light is sent into the optical cavity for a period of time as discussed above. Within the optical cavity there resides the vapor to be tested. Note that in the embodiments discussed herein, each vapor test is on a separate vapor batch and one or more tests may be run on the same batch preferably using the same flow rate for each sample. However, it is possible to design systems that allows for continuous processing, for example, by filling the cavity with a first batch of vapor from one portion of the film and then evacuating the cavity and refilling it with vapor from another portion of the film. After each refilling the cavity is filled with light and then the light is allowed to decay to determine the vapor content of each batch. The batches could be processed in real time as the film is being manufactured or when the film is about to be used for a device.

When the cavity has been filled with light for the proper amount of time (time T0, as shown in FIG. 2), process 302 causes the laser, or other energy source, to turn off under control of process 303.

Process 304, (as shown on FIG. 2), determines the lifetime of the decay time. If the light has a decay lifetime smaller than level T1 then process 304 determines that the water vapor is above a given limit, thus the tested film fails for use, process 305.

If, however, process 304 determines that the decay lifetime is greater than T1, this means that the amount of water in the chamber causing the lifetime decay is less than a critical amount. In a pass/no-pass system, the film then passes process 306. Optionally, even if the film fails for one purpose it might be acceptable for another purpose. In this regard, process 307 determines if the decay level at time T3 is below some set value. If so, the film is discarded. If not, process 308 allows the film to be used for other purposes. Multi-levels can be used to "grade" the film.

In some situations, it may be desired to use the film in some other application and thus it is desired to know exactly how much water vapor is present. In those cases, a quantitative method should be used, such as the one described in embodiment 40.

FIG. 4A shows another embodiment 40 of the concepts discussed herein. In this embodiment, the light wavelength is tuned to match the water vapor absorption (around 1392.5 nm). Other resonant wavelengths can also be used, for instance mid-infrared lasers can increase the sensitivity of the CRDS since water exhibits a higher absorption strength in this spectral region, other wavelengths can be 1450 nm, 1950 nm, 2900 nm. Light within the chamber forms an optical cavity by use of high reflective mirrors 47 and 47' in the well-known manner. The system uses fast electronics to measure the decay time within optical cavity 43 as the light leaving the chamber impacts upon detector 46. This then allows for the calculation of the water content in $ppb_v$ using the set of equations presented in table 1. FIG. 4B shows a representative decay curve that may be obtained from the system of FIG. 4A.

Note that in some situations as discussed above, different analytes (vapors) may be present and the laser (or other collimated energy source) can be frequency tuned to resonate with a selected analyte. This tuning can be changed from time to time (even during the measurement of a given sample) to allow the system to provide measurements for different vapors, if desired. For example, for $O_2$ the wavelengths can be 0.7596 um, 1.58 um, 1.27 um, 1.06 um, 0.69 um and 0.63 um. For $CO_2$, the wavelengths can be 4.3 um, 2.7 um, 2 um, 1.6 um and 1.4 um.

Useful equations used to determine water vapor content through CRDS:

TABLE 1

Optical equations in Cavity Ring-down Spectroscopy

First Measurement: $\tau_{zero} = \dfrac{d}{c(1-R)}$    No gas in cavity

Second Measurement: $\tau(v) = \dfrac{d}{c(1-R+\sigma(v)Nd)}$    Gas in cavity

Calculate Content: $N = \dfrac{1}{c\sigma(v)}\left(\dfrac{1}{\tau(v)} - \dfrac{1}{\tau_{zero}}\right)$ c—speed of light
σ—absorption cross section
d—cell length
τ—ring-down time
R—reflectivity of minor
v—laser frequency
N—molecular density (content)

The vapor to be measured is input to the chamber via inlet 44 and removed via outlet 45. Light source 41 is a laser light tuned to the desired frequency. A portion (in the example, 99%) of the light is sent to test chamber 43, while a portion is sent to reference cell 48 for detection by detector 49. Accurate wavelength control is preferred to ensure that the wavelength of the light source match the specific water absorption band for a resonant condition. Therefore the emission wavelength of the light source needs to be measured constantly. For instance, changes in temperature of the laser diode that is used as light source, can shift the emission wavelength (by modifying the effective index of refraction of the laser structure) of the laser, detuning it from the resonant condition. One way to ensure constant operation at the resonant wavelength is to add a reference cell (containing water) with a detector 49 as presented in FIG. 4A. If the wavelength coming from the laser source matches the resonant absorption of the water contained in the reference cell, no light or very little light will reach the detector, and resonant operation will be ensured.

The CRDS cell can be interfaced with a permeating chamber that hosts the barrier film to be analyzed as will be discussed below. The sensitivity/precision for water vapor can be as low as 0.4 $ppb_v$. This means that it is able to detect $3 \times 10^{-10}$ grams of water contained in a volume of one liter at 20° C. and 1 atm total pressure.

Figure 5:
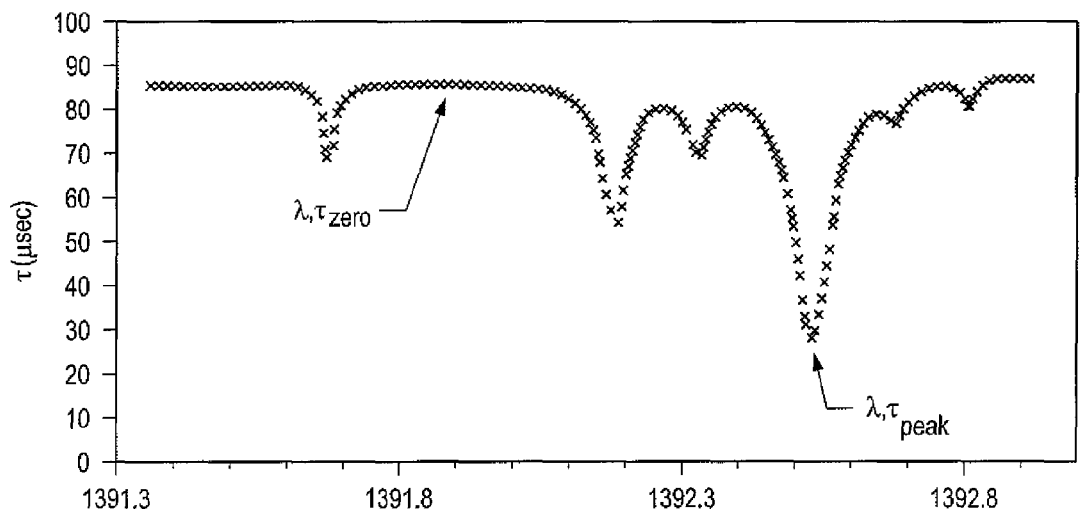
FIG. 5 shows a graph of water absorption peaks as a function of wavelength.

FIG. 5 shows a graph of water absorption peaks as a function of wavelength. As shown in this FIGURE and in order to measure the $\tau_{zero}$ of the cavity, a wavelength with no overlap with the water absorption peaks must be selected.

Figure 6:
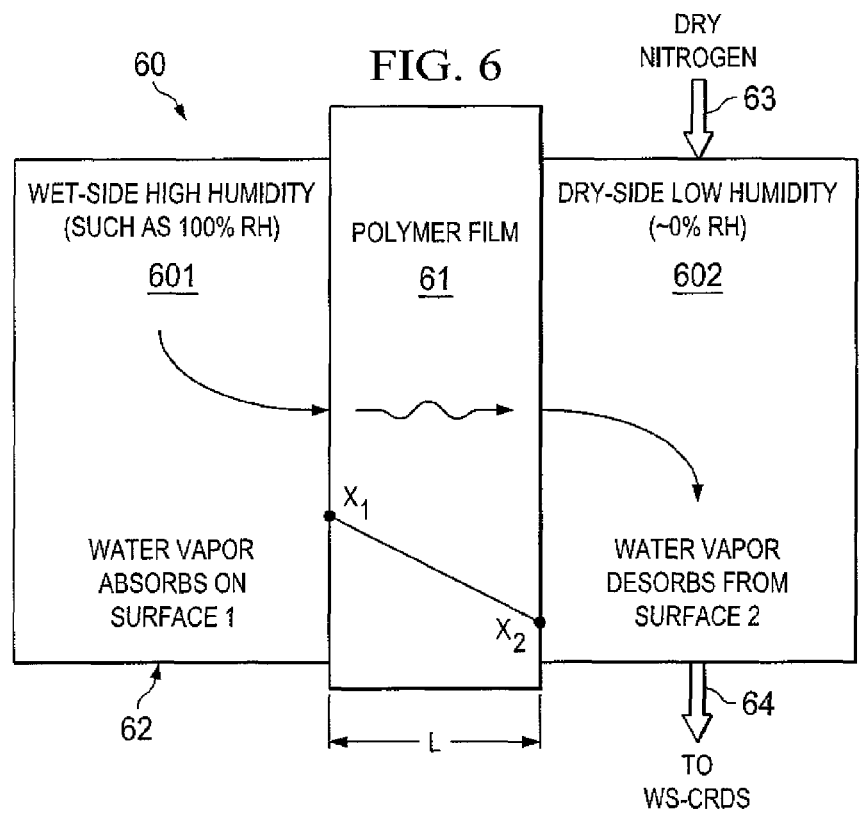
FIG. 6 shows one embodiment of a permeation cell.

FIG. 6 shows one embodiment of a permeation cell, such as cell 60. This allows for a method of measuring permeation rate through a film. The permeation cell is assembled such that a film, such as polymer film 61, is exposed to a controlled humidity on one side called the wet side (left side 601). The film is exposed to a dry carrier gas on the other side called the dry side (right side 602) via input 63. The carrier gas is typically nitrogen, but any carrier gas would work (helium produces the best results when water is the species to be detected). Over time, the moisture on wet side 601 adsorbs onto the polymer film, permeates through the film and then desorbs into the dry side carrier gas. Eventually the diffusion process reaches a steady-state permeation rate, typically in a few days depending on the thicknesses, absorptivities and diffusivities of the analyte gas, such as $H_2O$, $CO_2$, $O_2$, in the various layers in the film.

The dry nitrogen, now laden with the absorbed moisture from side 602, flows from the dry-side of the permeation cell via outlet 64 at a controlled rate to a CRDS test cell where its moisture content is analyzed as discussed above. The moisture content of the gas stream relates to the WVTR of the sample according to the following equation:

$$WVTR = C\dfrac{QP}{ART}MW$$

Where the variables refer to the following:
WVTR=Water Vapor Transmission Rate
C=Content ($ppb_v$) as measured by the CRDS
Q=Volume Flow Rate of Carrier Gas (Nitrogen) in CRDS cell
P=Total Pressure in CRDS cell
T=Temperature in CRDS cell
R=Universal Gas Constant
A=Surface Area of Test Film
MW=Molecular Weight of Carrier Gas (typically nitrogen)

This equation assumes that the gas on each side is ideal, that the flow rate is constant, that the nitrogen concentration is much greater than the water vapor content, and that the permeation rate has reached a steady state. Water vapor transmission is usually reported in g/($m^2$-day) and the CRDS reports the permeation in terms of parts per billion per volume ($ppb_v$). Two approaches can be followed to convert $ppb_v$ to g/($m^2$-day). The first approach is the mathematical description above that relates $ppb_v$ and g/($m^2$-day). The second approach relies on measuring a group of samples with known permeation rates in g/($m^2$-day) and building a calibration curve using the readings from the CRDS unit. Note that in order to build the calibration curve, a given pressure and flow rate must be chosen. The "flow" detection configuration develops around the best operation conditions in terms of pressure, temperature and flow rate so as to ensure the highest accuracy and lowest detection limit.

Figure 7:
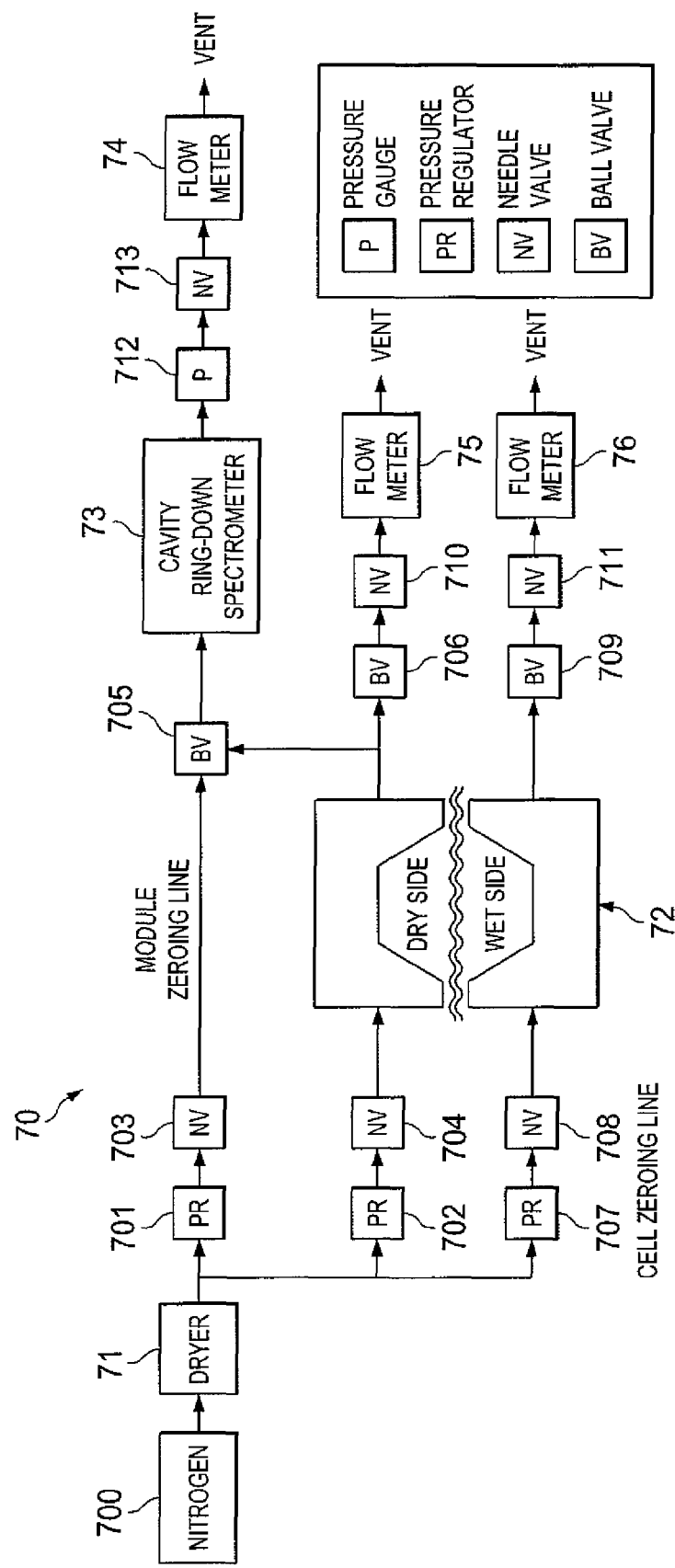
FIG. 7 shows one embodiment of a CRDS used in conjunction with the cell shown in FIG. 6.

FIG. 7 shows one embodiment 70 of a preferred arrangement of the system using the cell of FIG. 6. Ultra-High-Purity Nitrogen with low moisture content (such as 20 $ppb_v$) 700 is dried via dryer 71 and fed via pressure regulators 701, 702 and 707 and needle valves 704 and 708 both the dry and wet sides of the sample within chamber 72. This arrangement maintains equal pressure on both sides of the sample. The gas feeds to the cell should be isolated from one another, such as by using separate pressure regulators for each line as shown. The measured moisture content in the gas from the dry side constitutes the amount of moisture which has permeated through the film. This gas is then directed via ball valve 705 to cavity ring down measurement tool 73. Valves 706, 710, 709 and 711 as well as flow meters 75 and 76 are used to vent the chamber and to keep pressure constant.

For calibration, the input dry carrier can also be directed to tool 73 via regulator 701, valves 703, 705. This then compensates for moisture present in the feed nitrogen by allowing it to be subtracted out or taken into account in the decay timing.

The seal of the permeation cell around the sample is important. Leakage should be minimized. However, if moisture leaks through any of the seals in the system, it can be accounted for by subtracting the moisture content measured from the cell when no moisture is added to the wet side of the cell, from the measurement during normal operation in which moisture has been added to the wet-side of the cell.

Test Procedure

Prior to turning on the system shown in FIG. 6, there should be a sufficient amount of dry nitrogen carrier gas available. A new gas cylinder will typically read at around 2500 psi and cylinders must be replaced once the tank pressure on the regulator falls below 300-500 psi. The nitrogen line pressure should be set to 30 psi. The pressure regulators should be set to 15 psi.

The temperature of the test apparatus, including the valves fittings and CRDS, should be maintained at a constant level, typically room temperature such as 22° C. The temperature of the permeation cell may be at room temperature or another temperature if desired. The permeation cell can be heated or cooled using an oven, water bath, etc.

It is important to make sure all connections are properly tightened, leak tests are conducted, and gas streams have been purged. When this has been accomplished then turn 3-way valve 705 so that the CRDS is now being purged with gas from the zero line. Program and tune the system appropriately for the carrier gas and analyte of interest.

Select the appropriate sample film. Ensure that the film area is free of finger prints, grease, or any sort of damage. Cut a film specimen to shape using a suitable template and then trim the edges. Record the thickness of the film in millimeters.

Close needle valves 704 and 708 simultaneously. Open ball valves 706 and 709 at the cell outlets. Open the permeation cell and remove any previous sample and use Kimtech wipes to remove any old grease. Ensure that the O-ring gasket is securely seated in the cell. Reapply a new thin, smooth layer of silicone grease. Make certain that the sponge on the bottom of the permeation cell is moist and saturated with water.

Place the film sample onto the test cell by first orienting it so that it fits securely within the test fixture with the barrier facing towards the dry side. Ensure that the film sample is lying flat on the test cell, without any bubbles or wrinkles. Put the lid back onto the permeation cell and seal the remote cell by turning the knob to the right until lightly hand tight. Do not over-tighten the cell.

Open both needle valves 704 and 708 simultaneously. Confirm that the flow rates on wet and dry sides of the cell are equal using flow meters 75 and 76. Confirm that the pressures are equal on the regulators 702 and 707. If not, adjust both to 15 psig. Make sure that the cell is equally pressurized; otherwise it may result in damage to the film. If the pressure is too low, poor CRDS analysis may result. Close ball valve 709 on the wet side.

The permeation cell is now operating; however the CRDS is measuring the zero line only. Adjust needle valve 713 as necessary to achieve the desired flow rate for the experiment as read on flow meter 74. Once a stable zero line reading has been achieved, record the moisture content of the zero line as measured by the CRDS. This may require several hours or overnight.

Turn three-way valve 705 so that the CRDS is now measuring the sample line. Close sample line outlet ball valve 706. Adjust needle valve 713 as necessary to achieve the desired flow rate for the experiment as read on flow meter 74. Once a stable sample line reading has been achieved, record the moisture content of the sample line as measured by the CRDS. This may require several hours or overnight.

The process should be repeated several times. Once the process has reached steady state, the repeated readings will be consistent, and the final WVTR value can be computed.

The moisture content from the zero line should be subtracted from the moisture content of the sample line to determine the moisture content due to permeation through the sample. The WVTR value is calculated from this content using the above equation.

Figure 8:
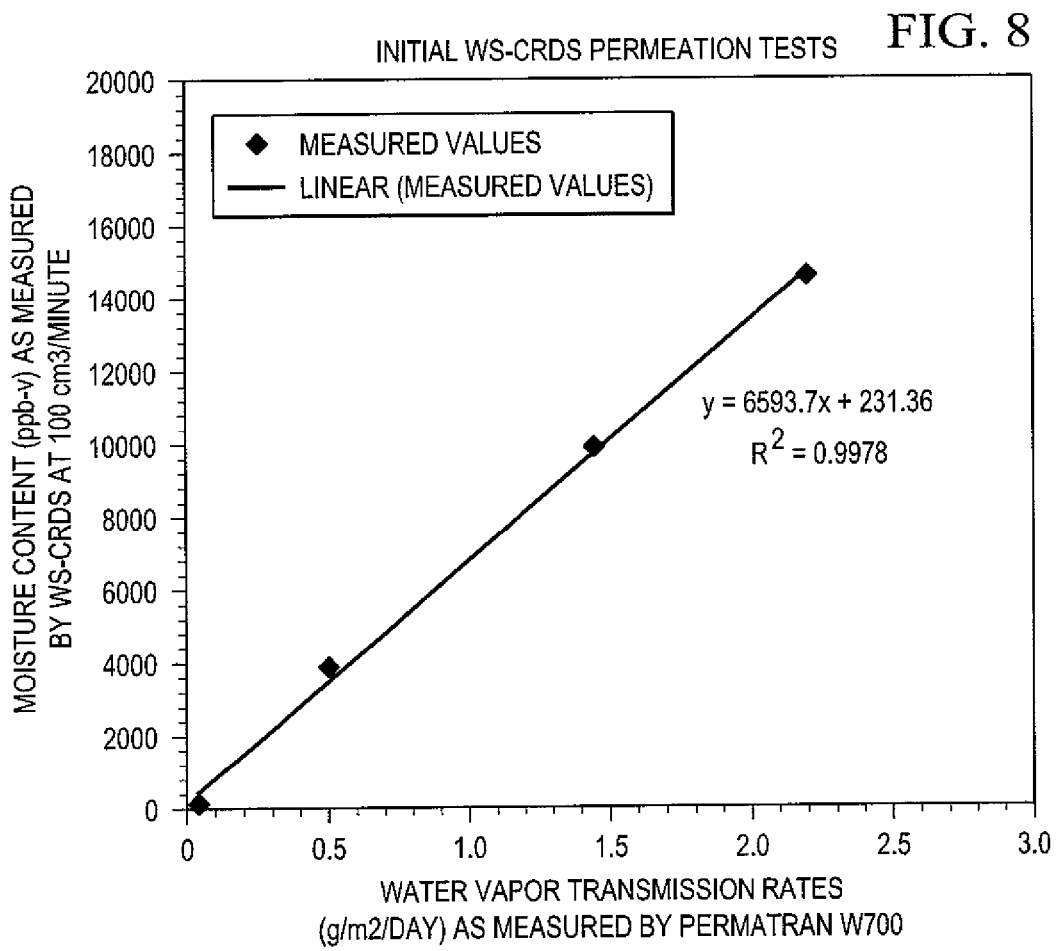
FIG. 8 shows a graph of actual test results using one embodiment of the invention.

FIG. 8 shows a graph of actual test results using one embodiment of the invention. The graph shows results of permeation tests with four different types of films performed with the CRDS using a flow rate of 100 $cm^3$/min, a pressure of 15 psi temperature of 23° C., and a file test area of 50 $cm^2$. The same films were measured with a Mocon Permatran instrument for comparison. The films are listed in Table 2.

TABLE 2

Comparison between CRDS and Mocon Permatran

| Sample Description | Moisture content at 23° C. as measured using CRDS ($ppb_v$) | WVTR at 23° C. as measured using Mocon Permatran W700, g/($m^2$-day) |
| --- | --- | --- |
| Polyester Film, 5.0-mil thickness, Mylar A from DuPont | 14598 | 2.210 |
| Polyester Film, 7.5-mil thickness, Mylar A from DuPont | 9886 | 1.494 |
| Barrier Film A, proprietary construction | 3894 | 0.531 |
| Barrier Film B, proprietary construction | 153.2 | 0.039 |

The results show very good, linear correlation between moisture content as measured using a CRDS detector and the permeation rate of each film as measured using a Mocon Permatran analyzer, which is the most widely used analyzer currently available. The results also show that a sample with a transmission rate of 1 g/($m^2$-day) produces a moisture content in our experiment of approximately 10,000 $ppb_v$ when tested at a flow rate of 100 $cm^3$/min.

Figure 9:
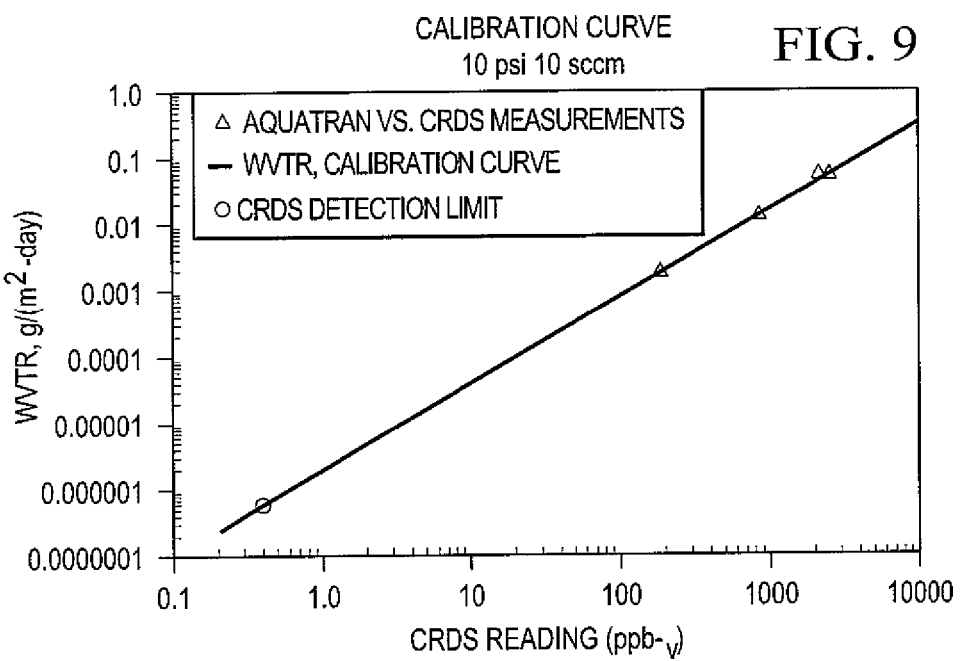
FIG. 9 shows a graph of actual test results using another embodiment of the invention.

FIG. 9 shows a graph of actual test results using another embodiment of the invention. The graph shows results of permeation tests with three different reference films, performed with the CRDS using a flow rate of 10 $cm^3$/min, a pressure of 10 psi, temperature of 23° C. and a film test area of 50 $cm^2$. The same reference films were measured with a Mocon Aquatran instrument for comparison. The graph also shows a calibration curve based on these measurements, and an extrapolation to the detection limit of the CRDS detector. Since the CRDS technique is capable of detecting moisture content as low as 0.4 ppb$_v$, we can deduce that transmission rates as low as $10^{-6}$ g/(m$^2$-day) can be detected. The films are listed in Table 3.

TABLE 3

Comparison between CRDS and Mocon Aquatran

| Sample Description | Moisture content at 23° C. as measured using CRDS (ppb$_v$) | WVTR at 23° C. as measured using Mocon Aquatran, g/(m$^2$-day) |
| --- | --- | --- |
| Black-Gold Reference Film | 192.8 | 0.002 |
| Green Reference Film | 902 | 0.014 |
| Blue Reference Film | 2500 | 0.059 |

Films with low permeation rates then can be used for construction of substrates and other elements of semiconductors where low permeation is required. Examples of films that can be tested using the concepts discussed herein are:
  Polyester Film (such as PET or PEN);
  Polyethylene Film (such as LDPE or HDPE);
  Polyethylene-Vinyl Acetate (EVA) film;
  Polypropylene (PP) Film;
  Polytetrafluoroethylene (PTFE) film;
  Ethylene-Tetrafluoroethylene Copolymer (ETFE) film;
  Fluoroethylene-propylene Copolymer (FEP) film;
  Polymethylmethacrylate (PMMA) film;
  Other similar polymer films;
  Polymer Films such as the ones above coated with one or more barrier layers such Al2O3, SiO2, TiO2, ZrO2, ITO, ATO, or other similar coatings;
  Polymer Films such as the ones above, but also coated with functional primers, adhesives, hard coatings or planarizing coatings;
  One or more Adhesive Laminations of the films above or similar films.

Note that in some situations, different gas vapors may be measured for permeation rate through a substance and when this is done the laser (or other collimated energy source) can be frequency tuned to resonate with the selected vapor. This tuning can be changed from time to time (even during the measurement of a given sample) to allow the system to provide measurements for different vapors, if desired. For water vapor, tuning could be, for example, 1392.5 nm, 2900 nm, 1950 nm, and 1450 nm, other analyte vapors could be, for example, CO$_2$ and O$_2$. For CO$_2$, the tuning could be 4.3 um, 2.7 um, 2 um, 1.6 um, 1.4 um. For O$_2$, the tuning could be 0.7596 um, 1.58 um, 1.27 um, 1.06 um, 0.69 um, 0.63 um. The carrier gas can be selected from the list of nitrogen, helium, argon, neon, xenon, krypton or air.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A method of determining a permeation rate measurement of a substance through a material; said substance impacting said material on a first surface and said measurement being a rate of movement of said substance through said material due to permeation of said substance through said material, said method comprising:
  placing a sampling of said substance from said first surface of said material in an optical cavity; and
  measuring a decay time of certain energy applied to said cavity against a known time of decay of said energy in an absence of said substance;
  wherein determining the measurement occurs without a vacuum.

2. The method of claim 1 wherein a wavelength of said certain energy is tuned to resonate with said substance within said cavity.

3. The method of claim 1 wherein said wave energy is a laser wavelength tuned so that said wavelength resonates with water vapor within said cavity.

4. The method of claim 3 wherein said tuning is at a wavelength selected from the following: 1392.5 nm, 1450 nm, 1950 nm, 2900 nm.

5. The method of claim 1 further comprising:
  calculating vapor content based upon said measured decay time.

6. The method of claim 5 wherein said cavity is part of a cavity ring-down spectroscopy technique.

7. The method of claim 2 wherein said substance is selected from: water, oxygen, carbon dioxide.

8. A system for measuring permeation rate through a film from a first surface to a second surface, said film having said first surface exposed to a vapor, said system comprising;
  an optical cavity;
  means for injecting into said cavity a sampling of atmosphere at said second surface of said film after said first surface has been exposed to said vapor; and
  a wave energy generator for generating energy for insertion into said cavity, said energy having a first decay time in the absence of said injected vapor and a measurable changed decay time in the presence of said injected vapor;
  wherein measuring the permeation rate occurs, without a vacuum.

9. The system of claim 8 further comprising;
  means for determining injected vapor content based upon said measured decay time.

10. The system of claim 9 further comprising:
  a pass/fail detector for determining acceptance in real-time of a film based upon said measured decay time.

11. The system of claim 9 wherein said wave energy generator is a laser tuned to resonate with said injected vapor.

12. The system of claim 9 wherein said injected vapor is selected from: water vapor, oxygen, carbon dioxide.

13. The system of claim 8 wherein said tuning is at a wavelength selected from the following: 1392.5 nm, 1450 nm, 2900 nm.

14. The system of claim 8 wherein said injecting means comprises:
  means for using a gas as a carrier for said sampling of said atmosphere; and
  means for removing from said gas unwanted moisture content.

15. A test apparatus for performing permeation testing of a film, said apparatus comprising:
- a permeation cell;
- means for supplying a dry carrier gas to a film contained within said cell, said gas being supplied to both a dry and wet side of said film;
- means for exposing said wet side of said film to a vapor;
- means for passing said gas from said dry side to an optic cavity, said gas acting as a carrier for any of said vapor from said wet side that permeated said film to said dry side;
- means for applying collimated energy to a resonance cavity for a determined time; and
- means for determining an amount of permeated vapor through said film by measuring a decay time of said energy beam at a completion of said determined time;
- wherein said means are carried out in the absence of a vacuum.

16. The apparatus of claim 15 wherein said vapor is water vapor and wherein said collimated energy is laser light.

17. The apparatus of claim 16 further comprising:
control for adjusting a wavelength of said laser tight to an optimal wavelength for resonation with an expected permeated vapor.

18. A electronic device comprising:
at least one substrate, said substrate subject to deterioration over time due to vapor permeating said substrate, said substrate protected by a film having a vapor harrier, said film having passed a test for low water vapor permeation, said test comprising using a list of acceptable energy delay times contained within a database, said delay times be used in conjunction with a cavity ring-down spectroscope (CRDS) for measuring water vapor transmission rate through said film;
wherein said measuring occurs without a vacuum.

19. The device of claim 18 wherein said vapor is selected from: water, oxygen, carbon dioxide.

20. The device of claim 18 wherein said CRDS uses a laser tuned to at least one of the following wavelengths:
1392.5 nm, 1450 nm, 2900 nm.

* * * * *